United States Patent [19]

Volman

[11] Patent Number: 5,152,372
[45] Date of Patent: Oct. 6, 1992

[54] INTEGRAL FILLER CAP AND CHIP DETECTOR FOR USE WITH A FLUID RETENTIVE HOUSING

[75] Inventor: Semion Volman, Jerusalem, Israel

[73] Assignee: Israel Aircraft Industries Ltd., Lod, Israel

[21] Appl. No.: 449,726

[22] Filed: Dec. 11, 1989

[30] Foreign Application Priority Data

Dec. 16, 1988 [IL] Israel .......................................... 88709

[51] Int. Cl.⁵ .............................................. F01M 1/10
[52] U.S. Cl. ................................. 184/6.25; 184/108; 340/631
[58] Field of Search ............... 184/6.12, 6.18, 6.25, 184/7.4, 88.1, 105.1, 104.1, 6.4, 108; 415/121.2, 118; 416/146 A; 340/631

[56] References Cited

U.S. PATENT DOCUMENTS

| | | | |
|---|---|---|---|
| 1,806,001 | 5/1931 | Simms | 184/6.25 |
| 2,462,715 | 2/1949 | Booth | 340/631 |
| 2,556,390 | 6/1951 | Harrison | 184/6.4 |
| 2,885,081 | 5/1959 | Stem | 184/6.25 |
| 3,457,504 | 7/1969 | Arthur et al. | 340/631 |
| 3,553,672 | 1/1971 | Smith | 340/631 |
| 4,731,578 | 3/1988 | Tsaparzis | 340/631 |

Primary Examiner—Ira S. Lazarus
Assistant Examiner—Alan B. Cariaso
Attorney, Agent, or Firm—Darby & Darby

[57] ABSTRACT

For use in conjunction with a fluid retentive housing defining a fluid volume and containing a lubricant, wherein there is provided a fluid port for the lubricant, an integral filler cap and metal debris detector assembly for removable placement within the fluid port comprising a filler cap defining an outer surface for insertion into the fluid port and further defining a bore and magnetic apparatus arranged within the bore and immersed in the fluid volume for attracting metal debris suspended in a lubricant fluid flow so as to remove metal debris from circulation.

13 Claims, 4 Drawing Sheets

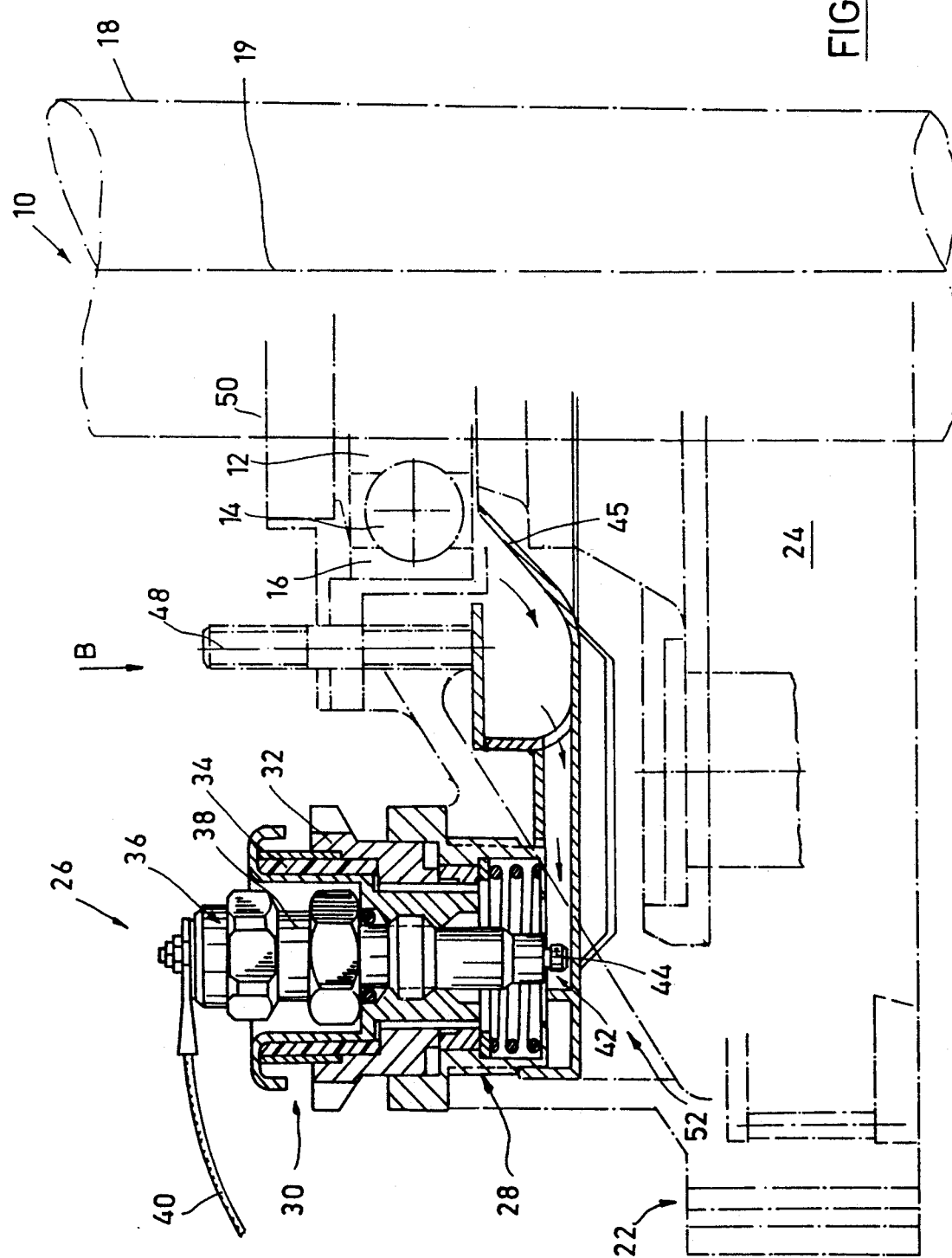

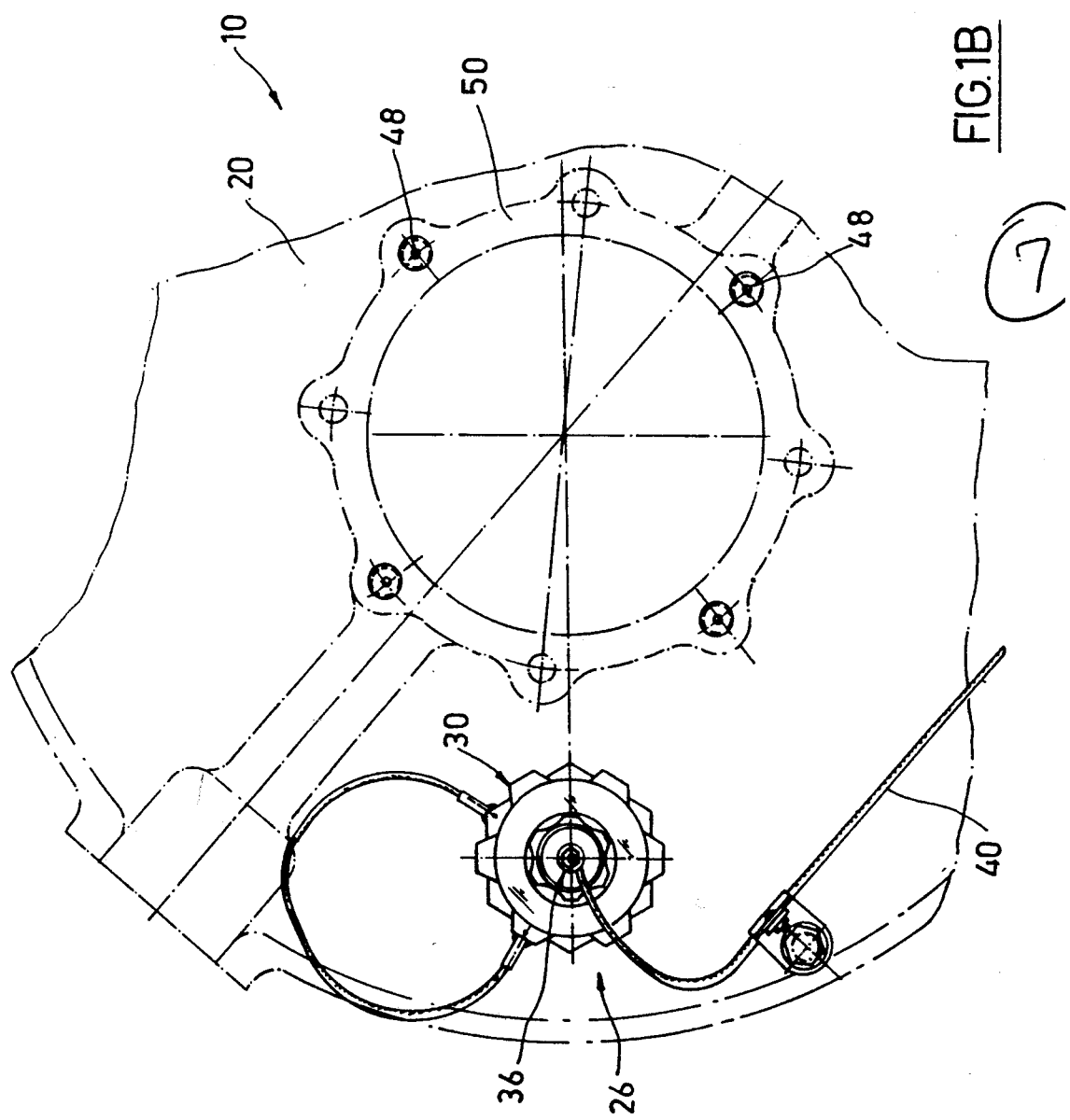

INTEGRAL FILLER CAP AND CHIP DETECTOR FOR USE WITH A FLUID RETENTIVE HOUSING

FIELD OF THE INVENTION

The present invention relates generally to helicopter main transmission assemblies and, in particular, to apparatus for detecting metal chips present in the lubrication system of such assemblies.

BACKGROUND OF THE INVENTION

The flight capability of a helicopter is provided largely by a main rotor, mounted onto a main rotor shaft. The main rotor shaft is rotated by the helicopter engine, via a main transmission assembly. The main transmission assembly cover, or top case assembly, defines an aperture through which the main shaft extends and onto which is mounted a main bearing. In a Bell 206 helicopter, for example, the main transmission assembly reduces the rate of revolutions of the engine, of about 6000 r.p.m. to the desired rotation rate of about 400 r.p.m. of the main shaft.

The main bearing and the transmission assembly are lubricated by a fluid which flows therethrough and which may be replenished via a filler neck assembly in which there is provided a removable filler cap. When the main rotor is in operation, the lubricant fluid flows in an outward and downward direction through the main transmission assembly, prior to passing, under centrifugal influence, inwards and upwards along the main shaft until it reaches the main bearing and outwards again, via a collector, and once again down towards the main transmission assembly.

In the main transmission assembly, wherein metal components, such as gear wheels, are continually meshing or otherwise making contact with each other, metal fragments tend to be chipped from the components. The chips further abrade the components thus creating yet more chips and so cause further deterioration of the transmission. Periodically, therefore, it may be necessary to replace worn components so as to facilitate continued efficient functioning of the transmission.

Furthermore, accumulation of metal chips could lead to clogging of lubricant passages within the transmission and lead to a reduced cooling thereof by the lubricant. In an extreme case, a continued accumulation of metal chips within the transmission could lead to a complete breakdown while the helicopter is in flight. It is, therefore, known to provide a chip detector in the top case assembly.

A conventional chip detector comprises a magnet and an electrode, electrically insulated from each other, mounted in the top case assembly so as to be exposed to the lubricant fluid flow. The provision of the chip detector within the top cover ensures that any chip will at some stage, be carried into association with the detector, due to the lubricant flow path described above.

As a metal chip in suspension in the fluid is attracted to the detector and contacts it, as it makes electrical contact with the electrode, a short circuit occurs. This facilitates the sending of a warning signal to the pilot.

Chip detectors are conventionally installed, for example, in the Bell 206 helicopter, in the top cover, which forms a main component of the top case assembly. This is achieved by modifying a top cover not originally having a chip detector so as to be able to receive a chip detector in a permanent mounting in contact with the lubricant flow.

It has been found that modification of the top cover as outlined above is very expensive and that it is not necessary to modify the top cover in order to provide an efficient, relatively low cost, chip detector mounting as required in helicopters.

SUMMARY OF THE INVENTION

It is an aim of the present invention to provide a combined filler cap and chip detector for the top case assembly of a helicopter so as to overcome disadvantages of the prior art.

There is provided, therefore, in accordance with a preferred embodiment of the invention, for use in conjunction with a fluid retentive housing defining a fluid volume and containing a lubricant, wherein there is provided a fluid port for the lubricant, an integral filler cap and metal debris detector assembly for removable placement within the fluid port comprising a filler cap defining an outer surface for insertion into the fluid port and further defining a bore and magnetic apparatus arranged within the bore and immersed in the fluid volume for attracting metal debris suspended in a lubricant fluid flow so as to remove metal debris from circulation.

Additionally in accordance with a preferred embodiment of the invention, there is also provided electrical apparatus associated with but electrically insulated from the magnetic apparatus for providing an electrical output when contacted by metal debris attracted by the magnetic apparatus.

Further in accordance with a preferred embodiment of the invention, the filler cap comprises an outer sleeve defining an outer surface for removable engagement with the fluid port and an inner surface and an inner sleeve defining an outer surface for engagement with the inner surface of the outer sleeve and an inner surface by which the bore is defined.

Additionally in accordance with a preferred embodiment of the invention, the inner surface of the outer sleeve and the outer surface of the inner sleeve together define a gas path, thus facilitating gas movement into or out from the fluid retentive housing in accordance with a decrease or increase in pressure within the fluid volume.

Further in accordance with a preferred embodiment of the invention, the magnetic apparatus and the electrical apparatus constitute a metal chip detection unit defining an outer surface complimentary to inner surface of the inner sleeve.

In accordance with an alternative embodiment of the invention, there is provided a top case assembly for a helicopter main transmission located within a fluid retentive housing defining a fluid volume comprising a top cover defining a lubricant fluid inlet and an integral filler cap and metal debris detector assembly for removable placement within the fluid inlet and at least partially immersed in the fluid volume.

Additionally in accordance with an embodiment of the invention, the integral filler cap and metal debris detector assembly comprises a filler cap defining an outer surface for insertion into the fluid inlet and further defining a bore and magnetic apparatus arranged within the bore and immersed in the fluid volume for attracting metal debris suspended in a lubricant fluid flow so as to remove the metal debris from circulation.

BRIEF DESCRIPTION OF THE DRAWINGS

The present invention will be understood and appreciated more fully from the following detailed description, taken in conjunction with the drawings, in which:

FIG. 1A is a sectional view of a portion of a top case assembly employing an integral filler cap and chip detector assembly, constructed and tested according to a preferred embodiment of the invention;

FIG. 1B is a partial plan view of the integral filler cap and chip detector of FIG. 1A, taken in the direction of arrow B therein;

DETAILED DESCRIPTION OF THE PREFERRED EMBODIMENT

Figure 3:
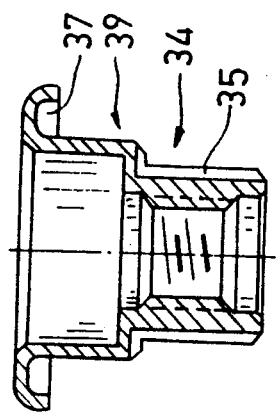
FIG. 3 is a sectional view of the inner plug shown in FIGS. 1A and 1B.

Reference is made to FIGS. 1A and 1B in which there is shown, indicated generally by reference numeral 10, a top case assembly for the main transmission (not shown) of a helicopter. Assembly 10 defines a main bearing comprising an inner race, bearings and an outer race, respectively referenced 12, 14 and 16, for a main rotor shaft, 18, passing therethrough.

Top case assembly 10 comprises a top cover 20 that is substantially symmetrical about axis of rotation 19 of shaft 18, and connected by bolts (not shown) to the main transmission housing (not shown) at locations 22. Together with the main transmission housing (not shown) assembly 10 defines a fluid volume 24 within which a lubricant is circulated.

A filler assembly 26 facilitates replenishment of the lubricant to volume 24 and comprises a filler neck assembly 28 defining a fluid inlet configured to receive an integral filler cap and chip detector assembly 30, constructed according to a preferred embodiment of the present invention.

The top case assembly 10 shown in FIGS. 1A and 1B is such as would be specifically intended for use with a Bell-206 helicopter. It will, however, be appreciated by persons skilled in the art that the integral filler cap and chip detector assembly 30 of the present invention is not limited to the precise configuration illustrated in the drawings and as specifically described below.

Figure 2A:
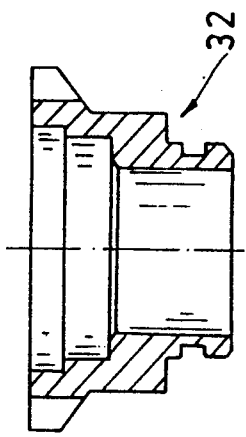
FIG. 2A is a sectional view of the outer plug shown in FIGS. 1A and 1B.
Figure 2B:
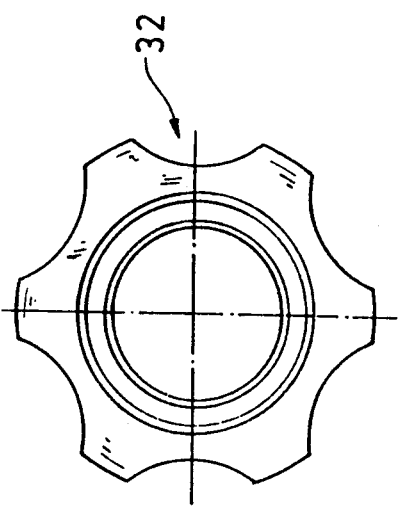
FIG. 2B is a plan view of the outer plug shown in FIG. 2A, taken in the direction of arrow B therein.

Assembly 30 comprises an outer plug 32, also shown in FIGS. 2A and 2B; an inner plug 34, also shown in FIG. 3; and a chip detector 36. Outer plug 32 has an external configuration such that it may be removably inserted into the fluid inlet defined by filler neck assembly 28 and it has an internal configuration such that inner plug 34 may be placed therein.

A particular design feature of assembly 30 (FIGS. 1A and 1B) is the presence of fluid flow paths (referenced in FIG. 3) defined by interconnecting grooves 35, 37 and 39 (not shown) formed on the outer surface of inner plug 34 (FIG. 3) and by the outer surface of outer plug 32. The flow paths thus formed permit 'breathing' to occur, air being permitted to enter or leave the main transmission housing (not shown) in accordance with a drop or rise in pressure within the housing.

Inner plug 34 has an internal configuration suitable for mounting therein chip detector 36, so that while not interfering with the normal function of the filler assembly 26, the chip detector is operative to detect substantially all metal chips circulated therepast.

The chip detector 36, which preferably, but not necessarily, is part No. B4429 manufactured by TEDECO of 24, E. Glenolden Ave., Glenolden, Pa. 19036, U.S.A., has two main functions, namely, removing metal debris or chips from the lubricant as it circulates past assembly 30 and providing an indication to a helicopter pilot of the presence of a chip within the main transmission.

The chip detector 36 comprises a typically elongate metal body 38 which, when supplied from an electrical power source, as shown schematically by a wire 40, functions as an electrode. A lower portion 42 of body 38 protrudes into fluid volume 24. Detector 36 also comprises a magnetic tip 44 extending from body 38 but electrically insulated therefrom and also protruding into the fluid volume.

An alternative sort of chip detector that is known is operative to destroy a detected metal chip by application of a high voltage thereto. This causes disintegration of the chip by burning.

Figure 4B:
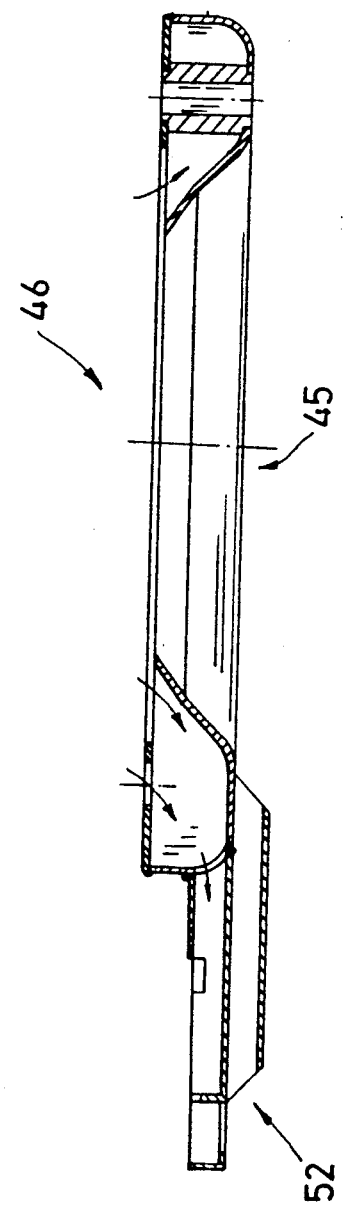
FIG. 4B is a sectional view of the collector shown in FIG. 4A, taken along line B—B therein.
Figure 4A:
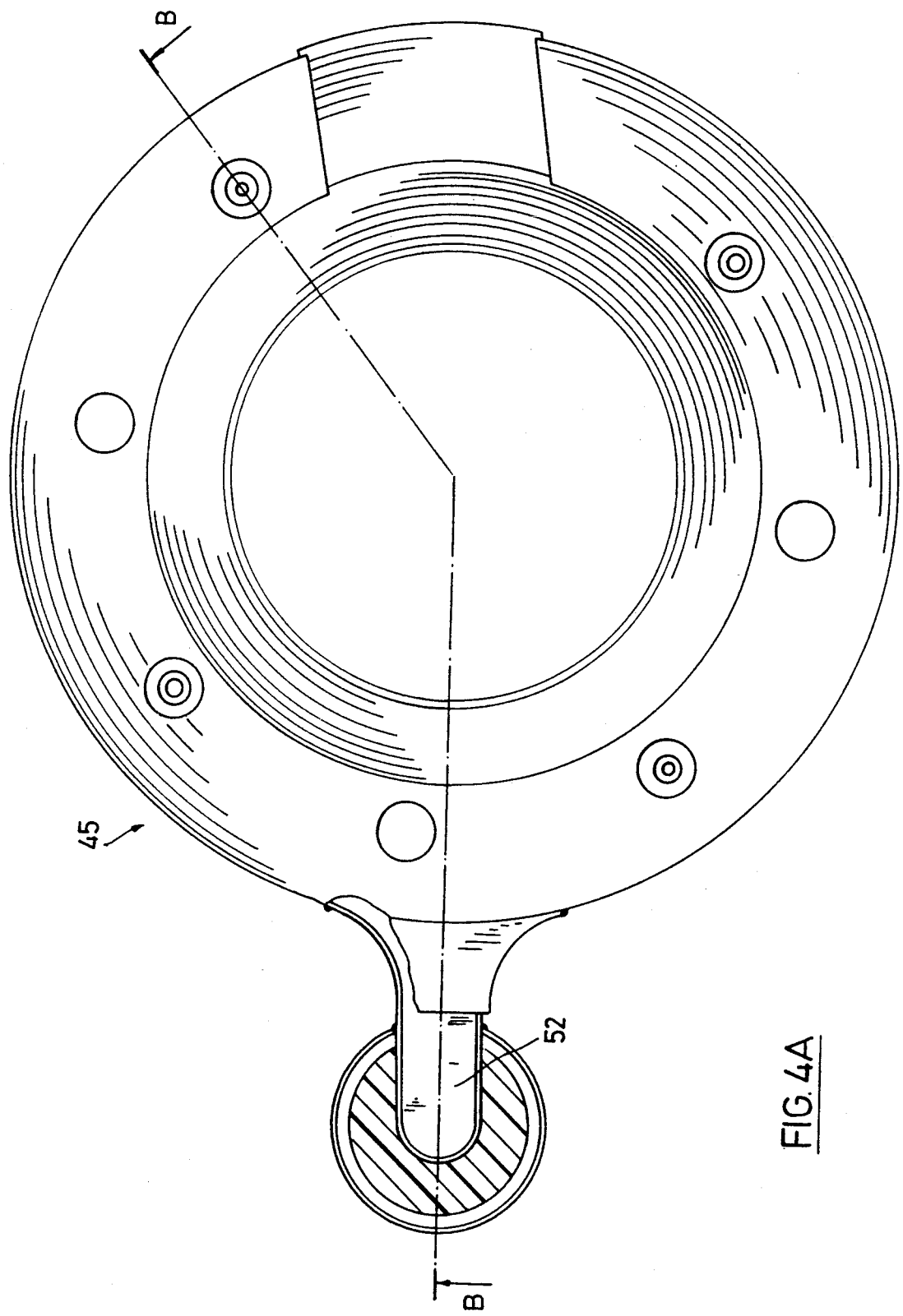
FIG. 4A is a plan view of the collector shown in FIG. 1B.

Reference is now made additionally to FIGS. 4A and 4B, in which there is shown a lubricant collector 45. Collector 45 is arranged within fluid volume 24 and defines a central aperture 46 through which rotor shaft 18 extends. Collector 45 is secured, by means of studs 48, to the top cover 20 and a main bearing cover 50.

Collector 45 is configured, as shown, to provide a desired flow path for the lubricant fluid. When the main rotor shaft 18 rotates, a centrifugal force is generated which draws the fluid inwards from the outer portions of the main transmission assembly and upwards along the rotor shaft and so as also to lubricate the main bearing. From the main bearing, the fluid flows outwards and is collected by collector 45 and circulated towards an outlet 52, from where the fluid flows downwards.

As fluid circulates towards outlet 52, it flows past the magnetic tip 44 of chip detector 36. Pieces of metal debris or metal chips are attracted to magnetic tip 44 and, as stated, when touching body 38, cause a warning signal to be generated, which is output via signal generating apparatus (not shown).

Referring once again to FIG. 1A, the shown chip detector, namely, Tedeco part no. B4429, was laboratory tested by the applicants in a collector having the cross-sectional configuration shown in the drawing, fitted with a top case assembly of Bell-206 helicopter. The helicopter motor was run at 6000 R.P.M. For the purposes of the test, the distance between magnetic tip 44 and an adjacent bottom portion 47 collector 45 was fixed at 3 mm.

Metal chips were fed into the oil and repeat tests were performed six times, each time the chips were detected and it was concluded that the chip detector as shown in FIG. 1A was performing efficiently.

It will be appreciated by persons skilled in the art that the present invention is not limited to what has been shown and described hereinabove by way of example. The scope of the present invention is limited, rather, solely by the claims which follow.

I claim:

1. For use in conjunction with a fluid retentive housing defining a fluid volume and containing a lubricant, wherein there is provided a fluid inlet for the lubricant, an integral filler cap and metal debris detector assembly for removable placement within the fluid inlet, comprising:
- an outer plug defining an outer surface for removable engagement with the fluid inlet and also defining an inner surface;
- an inner plug defining an outer surface for engagement with said inner surface of said outer plug and further defining a bore;
- magnetic means arranged within said bore and immersed in the fluid volume for attracting metal debris suspended in a lubricant fluid flow so as to remove metal debris from circulation; and
- electrical means associated with, but electrically insulated from, said magnetic means for providing an electrical output when contacted by metal debris attracted by said magnetic means, said inner surface of said outer plug and said outer surface of said inner plug together defining a gas path, thus facilitating gas movement into or out from the fluid retentive housing in accordance with a decrease or increase in pressure within the fluid volume.

2. An integral filler cap and metal debris detector assembly according to claim 1, and wherein said magnetic means and said electrical means constitute a metal debris detection unit defining an outer surface complimentary to said inner surface of said inner plug.

3. A top case assembly for a fluid retentive housing containing a helicopter main transmission and a circulating fluid lubricant, said top case assembly comprising:
- a top cover defining a lubricant fluid inlet;
- an integral filler cap and metal debris detector assembly for removable placement within the fluid inlet and partially immersed in said circulating fluid, said integral filler cap and metal debris detector assembly comprising:
  - a filler cap defining an outer surface for insertion into said fluid inlet and further defining a bore;
  - magnetic means, arranged within said bore so as to extend partially into the interior of said circulating fluid, for attracting and removing metal debris suspended in said circulating fluid; and
  - electrical means associated with, but electrically insulated from, said magnetic means for providing an electrical output when contacted by metal debris attracted by said magnetic means; and
- means for directing the circulating fluid toward said magnetic means and said electrical means of said integral filler cap and metal debris detector assembly.

4. A top case assembly according to claim 3, and wherein said filler cap comprises:
- an outer plug defining an outer surface for removable engagement with said fluid inlet and also defining an inner surface and
- an inner plug defining an outer surface for engagement with said inner surface of said outer plug and an inner surface defining said bore.

5. A top case assembly for a fluid retentive housing defining a fluid volume and containing a helicopter main transmission, said top case assembly comprising:
- a top cover defining a lubricant fluid inlet and
- an integral filler cap and metal debris detector assembly for removable placement within the fluid inlet and at least partially immersed in said fluid volume, said integral filler cap and metal debris detector assembly comprising:
  - an outer plug defining an outer surface for removable engagement with said fluid inlet and also defining an inner surface;
  - an inner plug defining an outer surface for engagement with said inner surface of said outer plug and an inner surface defining a bore;
  - magnetic means arranged within said bore and immersed in said fluid volume for attracting metal debris suspended in a lubricant fluid flow so as to remove the metal debris from circulation; and
  - electrical means associated with, but electrically insulated from, said magnetic means for providing an electrical output when contacted by metal debris attracted by said magnetic means, said inner surface of said outer plug and said outer surface of said inner plug together defining a gas path, thus facilitating gas movement into or out from the fluid retentive housing in accordance with a decrease or increase in pressure within the fluid volume.

6. A top case assembly for a fluid retentive housing defining a fluid volume and containing a helicopter main transmission, said top case assembly comprising:
- a top cover defining a lubricant fluid inlet;
- an integral filler cap and metal debris detector assembly for removable placement within the fluid inlet and at least partially immersed in said fluid volume; and
- means for diverting the lubricant fluid flow past said integral filler cap and metal debris detector assembly, said filler cap comprising:
  - an outer plug defining an outer surface for removable engagement with said fluid inlet and also defining an inner surface; and
  - an inner plug defining an outer surface for engagement with said inner surface of said outer plug and an inner surface by which said bore is defined, said inner surface of said outer plug and said outer surface of said inner plug together defining a gas path, thus facilitating gas movement into or out from the fluid retentive housing in accordance with a decrease or increase in pressure within the fluid volume.

7. A top case assembly for a fluid retentive housing defining a fluid volume and containing a helicopter main transmission, said top case assembly comprising:
- a top cover defining a lubricant fluid inlet;
- an integral filler cap and metal debris detector assembly for removable placement within the fluid inlet and at least partially immersed in said fluid volume, and
- means for diverting the lubricant fluid flow past said integral filler cap and metal debris detector assembly, said assembly comprising:
  - an outer plug defining an outer surface for removable engagement with said fluid inlet and also defining an inner surface,
  - an inner plug defining an outer surface for engagement with said inner surface of said outer plug and an inner surface by which said bore is defined, and
  - magnetic means arranged within said bore and immersed in said fluid volume for attracting metal debris suspended in a lubricant fluid flow so as to remove the metal debris from circulation, said inner surface of said outer plug and said outer surface of said inner plug together defining a gas path, thus facilitating gas movement into or out from the fluid retentive housing in accordance with a decrease or increase in pressure within the fluid volume.

8. A top case assembly for a fluid retentive housing defining a fluid volume and containing a helicopter main transmission, said top case assembly comprising:
a top cover defining a lubricant fluid inlet;
an integral filler cap and metal debris detector assembly for removable placement within the fluid inlet and at least partially immersed in said fluid volume; and
means for diverting the lubricant fluid flow past said integral filler cap and metal debris detector assembly, said assembly comprising:
an outer plug defining an outer surface for removable engagement with said fluid inlet and also defining an inner surface;
an inner plug defining an outer surface for engagement with said inner surface of said outer plug and an inner surface defining a bore;
magnetic means arranged within said bore and immersed in said fluid volume for attracting metal debris suspended in a lubricant fluid flow so as to remove the metal debris from circulation; and
electrical means associated with, but electrically insulated from, said magnetic means for providing an electrical output when contacted by metal debris attracted by said magnetic means; said inner surface of said outer plug and said outer surface of said inner plug together defining a gas path, thus facilitating gas movement into or out from the fluid retentive housing in accordance with a decrease or increase in pressure within the fluid volume.

9. A top case assembly according to claim 4, and wherein said magnetic means and said electrical means constitute a metal debris detection unit defining an outer surface configured for seating within said bore.

10. A top case assembly according to claim 5, and wherein said magnetic means and said electrical means constitute a metal debris detection unit defining an outer surface complimentary to said inner surface of said inner plug.

11. A top case assembly according to claim 6, and wherein said magnetic means and said electrical means constitute a metal debris detection unit defining an outer surface complimentary to said inner surface of said inner plug.

12. A top case assembly according to claim 7, and wherein said magnetic means and said electrical means constitute a metal debris detection unit defining an outer surface complimentary to said inner surface of said inner plug.

13. A top case assembly according to claim 8, and wherein said magnetic means and said electrical means constitute a metal debris detection unit defining an outer surface complimentary to said inner surface of said inner plug.

* * * * *